(12) United States Patent  (10) Patent No.: US 8,909,328 B2
Chon  (45) Date of Patent: Dec. 9, 2014

(54) SYSTEM AND METHOD FOR QUANTITATIVELY ASSESSING DIABETIC CARDIAC AUTONOMIC NEUROPATHY IN TYPE I DIABETIC BIOLOGICAL SUBJECT

(71) Applicant: Ki H. Chon, Worcester, MA (US)

(72) Inventor: Ki H. Chon, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 13/950,548

(22) Filed: Jul. 25, 2013

(65) Prior Publication Data

US 2014/0031651 A1  Jan. 30, 2014

Related U.S. Application Data

(60) Provisional application No. 61/675,502, filed on Jul. 25, 2012.

(51) Int. Cl.
   *A61B 5/04* (2006.01)
   *A61B 5/024* (2006.01)
   *A61B 5/0402* (2006.01)
   *A61B 5/00* (2006.01)
   *A61B 5/1455* (2006.01)

(52) U.S. Cl.
   CPC ........... *A61B 5/7275* (2013.01); *A61B 5/04012* (2013.01); *A61B 5/02405* (2013.01); *A61B 5/0402* (2013.01); *A61B 5/0006* (2013.01); *A61B 5/4035* (2013.01); *A61B 5/0059* (2013.01); *A61B 5/1455* (2013.01); *A61B 5/72* (2013.01); *A61B 5/742* (2013.01)
   USPC ........................................................ 600/509

(58) Field of Classification Search
   None
   See application file for complete search history.

(56) References Cited

U.S. PATENT DOCUMENTS

| | | | |
|---|---|---|---|
| 6,416,473 B1 * | 7/2002 | Risk et al. | 600/300 |
| 2009/0018404 A1 * | 1/2009 | Fendelander et al. | 600/301 |
| 2009/0318983 A1 * | 12/2009 | Armoundas et al. | 607/3 |

OTHER PUBLICATIONS

Bernardi, et.al., Methods of investigation for cardiac autonomic dysfunction in human research studies. Diabetes Metab. Res. Rev., 27: 654-664.*

Yang, et.al., Assessment of Diabetic Cardiac Autonomic Neuropathy in Type I Diabetic Mice. Conf Proc IEEE Eng Med Biol Soc. 2011;2011:6560-3.*

Zhong, et.al., Quantifying cardiac sympathetic and parasympathetic nervous activities using principal dynamic modes analysis of heart rate variability. Am J Physiol Heart Circ Physiol. Sep. 2006;291(3):H1475-83.*

* cited by examiner

*Primary Examiner* — Brian T Gedeon
*Assistant Examiner* — Ankit Tejani
(74) *Attorney, Agent, or Firm* — Burns & Levinson LLP; Jacob N. Erlich; Orlando Lopez

(57) ABSTRACT

The present disclosure provides a method and an apparatus for identifying development of diabetic cardiovascular autonomic neuropathy (DCAN) in a biological subject. In one aspect, the method includes collecting data associated with heart rates of a biological subject, and processing the collected data to extract primary and secondary components of the collected data by performing a principal dynamic mode (PDM) analysis. A significant reduction of the primary or secondary component at a predetermined time period can be indicative of the DCAN development.

24 Claims, 12 Drawing Sheets

SYSTEM AND METHOD FOR QUANTITATIVELY ASSESSING DIABETIC CARDIAC AUTONOMIC NEUROPATHY IN TYPE I DIABETIC BIOLOGICAL SUBJECT

CROSS-REFERENCE TO RELATED APPLICATIONS

This application claims the benefit of priority to U.S. Provisional Application No. 61/675,502, entitled QUANTITATIVE METHOD FOR DIABETIC CARDIAC AUTONOMIC NEUROPATHY ASSESSMENT IN TYPE I DIABETIC MICE, filed on Jul. 25, 2012, the entire contents of which are incorporated herein by reference.

The present invention also relates to U.S. Non-Provisional application Ser. No. 13/354,941, entitled PHYSIOLOGICAL PARAMETER MONITORING WITH A MOBILE COMMUNICATION DEVICE, filed Jan. 20, 2012, the entire contents of which are incorporated herein by reference.

BACKGROUND

The present invention relates to a system and a method for quantitatively assessing diabetic cardiac autonomic neuropathy (DCAN) in type I diabetic biological subject. More particularly, the present invention relates to a system and a method for quantitatively assessing DCAN in type I diabetic biological subject based on Principal Dynamic Mode (PDM) analysis.

DCAN is one of the most overlooked of all serious diabetes complications, and it can cause abnormalities in heart rate control as well as central and peripheral vascular dynamics. Consequences of DCAN include exercise intolerance, intraoperative cardiovascular lability, orthostatic hypotension, myocardial ischemia, increased risk of mortality and morbidity, and reduced quality of life, for persons with diabetes. One useful noninvasive method to assess autonomic function in various physiological and pathophysiological conditions, including evaluation of the autonomic dysfunction in diabetic subjects, is the use of heart rate variability (HRV). HRV is a marker of sympathetic and parasympathetic (vagal) influences on the modulation of heart rate. Reduced heart rate variability is known to be one of the earliest indicators of DCAN as DCAN has been shown to involve an imbalance of the autonomic nervous system (ANS). A recent study examining the effect of sustained hyperinsulinemic hypoglycemia on cardiovascular autonomic regulation in type I diabetics and their non-diabetic counterparts has found reduced cardiac vagal outflow in all patients. Another study, examining HRV changes in diabetes, has found that decreases in autonomic function are present early in the development of diabetes and that diabetes leads to a progressive decline in autonomic function. Whereas the DCAN Subcommittee of the Toronto Diabetic Neuropathy Expert Group identified heart rate variability, baroreflex sensitivity, muscle sympathetic nerve activity, plasma catecholamines, and heart sympathetic imaging as the most sensitive and specific approaches currently available to evaluate DCAN in clinical research, it also identified serious limitations of the existing methods and emphasized that efforts should be undertaken to develop new non-invasive and safe DCAN tests, with a higher sensitivity and specificity.

The limitations of the existing methods for evaluation of DCAN are clearly seen in experimental studies. For example, young streptozotocin (STZ)-diabetic rats exhibit a significant reductions in both heart rate and HRV, suggesting disturbance in the ANS balance. Further, insulin treatment of these STZ-treated diabetic rats showed no significant recovery of the autonomic nervous activity even though heart rate recovered to the state recorded prior to STZ administration. This is in agreement with clinical studies identifying limitations of heart rate variability as a diagnostic marker of DCAN. Apparently, new quantitative methods for assessment of this diabetic complication are needed.

In recent years, multiple, quite sophisticated, studies of pathogenetic mechanisms of diabetic peripheral neuropathy were conducted in mouse models, in contrast, investigations of DCAN leading to discovery of the important roles of the sorbitol pathway of glucose metabolism, impaired neurotrophic support, and mitochondrial dysfunction and bioenergetics have been performed in the rat. The literature on DCAN in mice is sparse, although a recent study in streptozotocin-diabetic mice identified the important role for the cyclooxygenase pathway. One intriguing mouse model of Type I diabetes is the Akita mouse. Ins2C96Y Akita mice, which spontaneously develop insulin-dependent diabetes at about 4 weeks of age, express a mutant non-functional insulin isoform. Four month-old Akita mice displayed sensory nerve conduction velocity deficit, thermal and mechanical hypoalgesia, tactile allodynia, as well as gait disturbances, in addition to sensory neuropathy, 5 month-old Akita mice develop motor nerve conduction velocity deficit and axonal atrophy of large myelinated fibers (dropout of large axons). Akita mice also show markedly impaired corpus cavernosum nitrergic nerve and sinusiodal endothelium function. Dystrophic changes have been noted for superior mesenteric and celiac ganglia. A further investigation provided evidence for cardiac parasympathetic dysfunction. Thus, there is a strong rationale to suggest that Akita mice develop DCAN similar to those found in STZ-diabetic rodents, and can be a suitable model for studying this complication.

SUMMARY

Diabetic cardiac autonomic neuropathy (DCAN) is one of the most common complications of diabetes. One reason why the pathogenesis of DCAN is unclear is that non-invasive assessment of DCAN in humans and animals has been problematic. To overcome this limitation, a sensitive and non-invasive method may be utilized to assess cardiac autonomic dysregulation from ECG and pulse oximeter recordings from mice. The method, which is easily applicable to humans, is based on principal dynamic mode (PDM) analysis of heart rate variability (HRV). The method is unique, in that it is able to separately identify the activities of the parasympathetic and sympathetic nervous systems without pharmacological intervention. In one embodiment, ECG is measured via telemetry in conscious 4 month old C57/BL6 control mice and in Akita mice, a model of insulin-dependent type 1 diabetes. The results indicate significant cardiac autonomic impairment in the diabetic mice in comparison to the controls. Both immunohistochemical and Western blot analyses show a reduction in nerve density in Akita mice as compared to the control mice, thus, corroborating PDM data analysis of HRV records. In addition, when tall-cuff pulse oximeter recordings are collected, starting from L5 months of age in both the C57/Bl6 controls and the Akita mice, onset of DCAN can be seen at 3 months in the Akita mice, which may persist up to the termination of the recording at 5 months. Western blot analysis of autonomic nerve proteins indicates a reduction in nerve density at 3 and 4 months, corroborating the pulse oximeter-based HRV analysis via the PDM approach. In contrast, traditional HRV analyses on both ECG and pulse oximeter recordings (based on either the power spectral density or time-domain measures) fail to detect the nerve rarefaction.

One objective of the present invention is to determine if DCAN in Akita mice can be monitored with PDM analysis of HRV. The PDM algorithm is shown to accurately separate the dynamics of the sympathetic and parasympathetic nervous systems. Which has not been possible using the estimation of low- and high-frequency spectral powers in the frequency bands between 0.04-0.15 Hz and 0.15-0.4 Hz, respectively. Therefore, the onset and the progression of DCAN in Akita mice are monitored with PDM and compared its performance to the standard time-domain HRV parameters and spectral analysis techniques. The present invention involves male Akita and age-matched C57/BL6 controls from which ECG and pulsatile blood flow records are collected via telemetry and tail-cuff pulse oximetry, respectively. The pulse oximeter is used on 1.5-4 month old mice while ECG electrodes are used for 4-5 month old mice. The results of the ECG and pulse oximeter analyses are correlated with the results from an immunohistochemical staining study and Western blot assessments of cardiac autonomic innervation.

According to one aspect, the present invention provides a method for identifying development of diabetic cardiovascular autonomic neuropathy (DCAN) in a biological subject. The method comprises collecting data associated with heart rates of a biological subject, and processing the collected data to extract primary and secondary components of the collected data by performing a principal dynamic mode (PDM) analysis, wherein a significant reduction of the primary or secondary component at a predetermined time period is indicative of the DCAN development. The primary and secondary components respectively represent sympathetic and parasympathetic dynamics of an autonomic nervous system of the biological subject.

In one embodiment, collecting the data comprises monitoring pulsatile signals associated with the heart rates of the biological subject by detecting an optical property associated with a biological fluid of the biological subject using a video camera of a portable communication device. In an alternative embodiment, collecting the data comprises monitoring pulsatile signals associated with the heart rates of the biological subject by using an electrocardiography (ECG) device.

In one embodiment, processing the collected data comprises using a device, a portable communication device in one instance, to detrend the collected data to obtain output data, delay the detrended data by one unit to obtain input data, form a principal matrix using Volterra kernels based on the input and the output, and eigendecompose the principal matrix using a predetermined number of orthonormal functions as a basis to obtain eigenvalues and eigenvectors of the principal matrix. The primary and secondary components respectively correspond to two of the eigenvectors associated with the first two greatest eigenvalues of the principal matrix. The orthonormal functions comprise Laguerre functions.

In one embodiment, collecting the data comprises collecting the data while the biological subject is at an active state, and a significant reduction of the primary component is indicative of the DCAN development. In an alternative embodiment, collecting the data comprises collecting the data while the biological subject is at a quiet state, and a significant reduction of the secondary component is indicative of the DCAN development.

According to another aspect, the present invention provides a device, a portable communication device in one instance, for identifying development of diabetic cardiovascular autonomic neuropathy (DCAN) in a biological subject. The a device, a portable communication device in one instance, comprises a processor configured to collect data associated with heart rates of a biological subject, and a memory coupled to the processor to store the collected data; wherein the processor is further configured to process the collected data to extract primary and secondary components of the collected data by performing a principal dynamic mode (PDM) analysis, wherein a significant reduction of the primary or secondary component at a predetermined time period is indicative of the DCAN development.

In one embodiment, the portable electronic device further comprises a video camera coupled to the processor, the video camera being configured to obtain pulsatile signals associated with the heart rates of the biological subject. The video camera is further configured to detect an optical property associated with a biological fluid of the biological subject so as to obtain the pulsatile signals. In an alternative embodiment, the device, a portable communication device in one instance, further comprises an electrocardiography (ECG) device configured to obtain pulsatile signals associated with the heart rates of the biological subject.

In one embodiment, the processor is further configured to detrend the collected data to obtain output data; delay the detrended data by one unit to obtain input data; form a principal matrix using Volterra kernels based on the input and the output; and eigendecompose the principal matrix using a predetermined number of orthonormal functions as a basis to obtain eigenvalues and eigenvectors of the principal matrix. The primary and secondary components respectively correspond to two of the eigenvectors associated with the first two greatest eigenvalues of the principal matrix, and the orthonormal functions comprise Laguerre functions.

In one embodiment, the portable electronic device further comprises a display screen configured to display an indication of the DCAN development, if the processor collect the data while the biological subject is at an active state, and if a significant reduction of the primary component occur. In an alternative embodiment, the portable electronic device further comprises a display screen configured to display an indication of the DCAN development, if the processor collect the data while the biological subject is at a quiet state, and if a significant reduction of the secondary component occur.

DETAILED DESCRIPTION

Figure 1A:
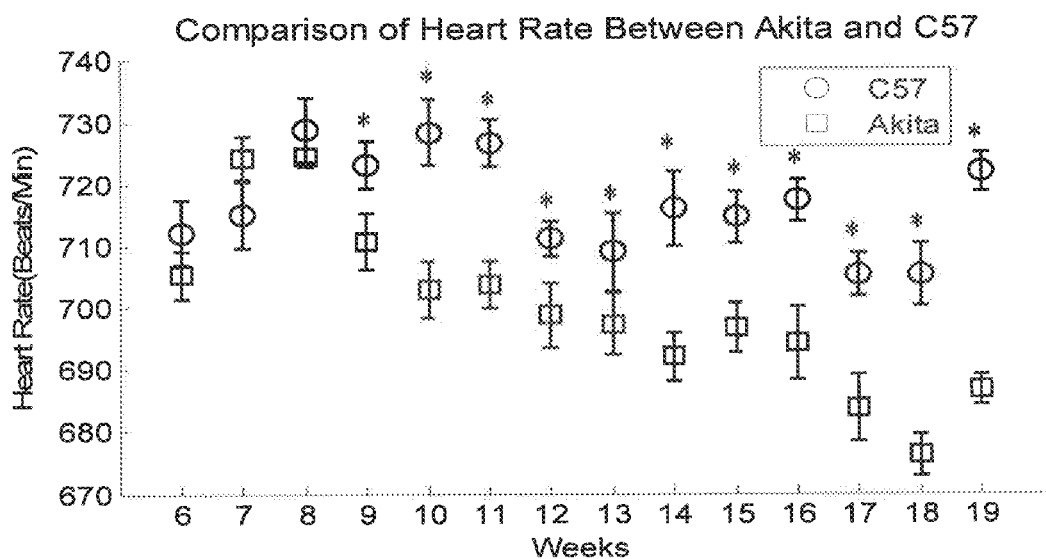
FIG. 1A illustrates the comparison of heart rate between Akita and wild-type mice, the data being recorded from a pulse oximeter.

A portion of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

The following detailed description presents the currently contemplated modes of carrying out the invention. The description is not to be taken in a limiting sense, but is made merely for the purpose of illustrating the general principles of the invention, since the scope of the invention is best defined by the claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

EXPERIMENTS

Below Table 1 summarizes all in vivo and ex vivo measurements that were performed. The table keys include: (i) measurement; (ii) age of mice; (iii) quantity and type; (iv) state. The Case lettering below corresponds to the labels in Table 1.

TABLE 1

| Experimental Data | | | |
|---|---|---|---|
| In Vivo Measurements | | | |
| A | (i) ECG Telemetry<br>(ii) 4 months; 5 months<br>(iii) 5 Akita; 5 wild-type<br>(iv) Inactive (sleeping) | B | (i) Tail-cuff Pulse Oximetry (PPG)<br>(ii) 1.5 months; 5 months<br>(iii) 5 Akita; 5 wild-type<br>(iv) Active |

TABLE 1-continued

| Experimental Data | | | |
|---|---|---|---|
| Ex Vivo Measurements | | | |
| C | (i) Western blot<br>(ii) 2 months<br>(iii) 5 Akita, 5 wild-type | D | (i) Western blot<br>(ii) 3 months<br>(iii) 5 Akita, 5 wild-type |
| E | (i) Western blot<br>(ii) 4 months<br>(iii) 5 Akita, 5 wild-type | F | (i) Immunohistochemical staining<br>(ii) 4 months<br>(iii) 5 Akita, 5 wild-type |

Details regarding the heart rate variability data analyses performed on in vivo measurements are provided in below Table 2.

TABLE 2

| Heart Rate Variability (HRV) Analysis | |
|---|---|
| Principal Dynamic Modes (PDM)<br>Provides sympathetic, parasympathetic, symp/parasymp ratio | |
| PDM of A | PDM of B |
| Power Spectral Density (PSD)<br>Provides LH, HF, LF/HF ratio | |
| PSD of A | PSD of B |
| Time Domain Measures<br>SDNN - provides sympathetic & parasympathetic<br>RMSSD - provides parasympathetic only | |
| SDNN of A<br>RMSSD of A | SDNN of B<br>RMSSD of B |

Case A: Telemetry ECG Transmitter Implantation and Data Collection

In this embodiment, experiments are performed on age-matched 4 month old male C57BL/6 (wild type; n=5) and Akita (n=5) mice. All animal-related experimental protocols are approved by the institutional Animal Care and Use Committee at Stony Brook University of New York and Worcester Polytechnic institute of Massachusetts. The surgery is conducted in accordance with Division of Laboratory Animal Resources guidelines. The mice are first anesthetized in a chamber with isoflurane and maintained under anesthesia with 1% isoflurane in 50% oxygen/50% nitrogen and maintained 0.8% to 1.5% isoflurane throughout the experiment to maintain the anesthetic state. A wireless ECG transmitter is then embedded subcutaneously on the dorsal side of the animal, and wired electrodes are threaded under their skin to reach the position of Einthoven bipolar lead II configuration and then sutured to the body wall. The activity of each animal is recorded via, an animal activity meter (commercially available from, for example, Columbus Instruments Inc., Columbus, Ohio). Activity recordings are used to help identifying data segments that are captured during a quiet state so that motion and noise artifacts are minimized in the analysis. A determination of each mouse's activity is made by scanning an infrared beam at 160 Hz. The sensor beams are spaced every 0.5 inches (1.27 cm) in the mouse's cage and the number of beam interruptions in the X, Y and Z axes are recorded, ECO and activity data are collected after one week's recovery and continuously recorded for 1 month.

ECG Data Processing and Analysis

The measurement differences between Akita and C57BL/6 mice are compared on a weekly basis for a duration of 1 month (4 weeks). For each day, a 15 minute data segment is selected from the animals' sleep stage and the results are averaged based on every 1 minute interval of data. Both heart rate and activity data are examined to make sure that all selected data segments are during a quiet condition. To ascertain that the choice of a data segment is representative of all data during quiet states, two other arbitrarily-chosen 15 minute segments are also selected and analyzed using the same data analysis protocol as described above. Data may be analyzed using Matlab R2010a (commercially available from the Mathworks, Natick, Mass.), R-R interval series are obtained from ECG recordings using an R-wave detection software program. Automatic detection of the R-R series is carried out after removing erroneous spikes and premature beats, and then R-R intervals are subjected to the cubic spline procedure to make them equally spaced. The resultant heart rate time series are down-sampled to 10 Hz. Prior to HRV analysis, all data are detrended, zero-meaned, and normalized to unit variance.

Case B: Tail-Cuff Pulse Oximeter Data Collection and Analysis

In this embodiment, the mice are conscious and restrained in a tube-shaped mouse restrainer with their tails exposed. The mice are trained to be acclimated in the mouse restrainer for 30 minutes per day for a period of 1 week. Starting the following week, the mice are again placed in the restrainer for 30-60 minutes per day, and data are collected during their awake state. This is in contrast to telemetry ECG data which are collected during a quiet/sleep state to minimize noise artifacts. The mice are placed on a heating pad and the temperature is adjusted as needed to maintain a temperature at, for example, a normal body temperature of about 37° C. The Y-clip photoplethysmogram (PPG) sensor is laced on the proximal (thickest) portion of the tail to produce the best signal. Ten minutes of settling time is allowed so that a mouse can get used to the restrainer and Y-clip PPG sensor prior to the start of data collection, PPG data from sex- and age-matched mice are collected for only 30 minutes to 1 hour each day, 5 days a week. There are ten 1.5 month old mice in total (5 Akita and 5 C57BL/6) at the start of the experiment. The entire recording process lasts until the mice reach 5 months of age. PPG data are recorded at a sampling rate of 600 Hz.

Pulse Oximeter Data Processing and Analysis

For each day, a 15 minute data segment that is relatively free from motion and noise artifacts is selected. Data analysis is performed on every minute of data in the entire 15 minute segment, and the 15 results are averaged. In the time domain, to obtain heart beat intervals, a custom peak detection algorithm can be used. From pulse-interval series, an instantaneous heart rate signal (HR) is created at a sampling rate of 10 Hz using a previously-described technique. Both mean and trends are removed from the instantaneous HR signal, and data are normalized to unit variance.

Traditional Heart Rate Variability Analysis for ECG and Pulse Oximeter Recorded Data The mean heart rate, standard deviation of the normal-to-normal (SDNN), and root mean square of successive difference (RMSSD) parameters are calculated from the R-R interval series derived from both ECG and pulse oximeter recordings. SDNN reflects overall autonomic nervous activities and RMSSD reflects the parasympathetic dynamics. Prior to calculation of frequency domain measures, each HRV segment is zero meaned, detrended, and normalized to unit variance. In addition, the Welch periodogram was computed (a 256-point FFT with a Hanning window and 50% overlapping segments), calculated spectral powers in both the low frequency (LF) (0.4-1 Hz) band and high frequency (HF) (1-4 Hz) band as these frequency bands for mice have been determined in previous studies. It is well established that the LF band represents both sympathetic and parasympathetic nervous activities, while the HF band represents parasympathetic nervous activity. The LF/HF ratio is also computed to assess the autonomic balance of the C57BL/6 and Akita mice.

Principle Dynamic Mode (PDM) Analysis of HRV Obtained from ECG and Pulse Oximeter The Principle Dynamic Mode (PDM) is compared to the traditional HRV measures. The advantages of PDM have been documented and one of its salient features is that it enables accurate separation of the sympathetic and parasympathetic dynamics. The power spectrum of the HRV signal contains many different frequency peaks. For example, in humans, there are a very low frequency peak (0.01-0.04 Hz), mid-frequency peaks (0.04-0.15 Hz), high-frequency peaks (0.15-0.4 Hz), and a frequency peak beyond 0.4 Hz, which can be considered noise. Among these, some frequency components are more dominant than the others as represented by the spectral magnitudes. The main problem with power spectrum density (PSD) is that it is a linear method and cannot separate the sympathetic and parasympathetic dynamics, since the latter encompasses both the low and high frequency ranges. In contrast, the PDM takes into account the $2^{nd}$-order nonlinearities of HR dynamics and among many frequencies in the HRV signal, extracts the principal components using an eigen-decomposition approach. The two principal components extracted (those with the largest eigenvalues and their associated eigenvectors) represent sympathetic and parasympathetic dynamics, since they have significant magnitudes at the low, and low and high frequency bands, respectively. Further, these two principal components account for at least 80% of the entire dynamics. The feasibility of separation of the ANS dynamics via the PDM has been validated using ANS pharmacological blockades in a previous study.

The PDM method is based on the concept of extracting only principal dynamic components of the signal via eigen decomposition. The PDMs may be calculated using Volterra-Wiener kernels based on expansion of Laguerre polynomials. Among all possible choices of expansion bases, some require the minimum number of basis functions to achieve a given mean-square approximation of the system output. This minimum set of basis functions is termed the principal dynamic modes of the nonlinear system. The PDM specifically accounts for the inherently nonlinear dynamics of heart rate control, which the current PSD method is unable to do. A minimum set of basis functions is determined using the principal component analysis method, where the dominant eigenvectors and eigenvalues are retained as they relate more closely to the true characteristics of the signal. Non-dominant eigenvectors and eigenvalues represent noise or nonessential characteristics. Thus, principal component analysis separates only the essential dynamic characteristics from a signal that is corrupted by noise. In the case of the heart rate signal, the dominant eigenvectors and eigenvalues should reflect the dynamics of the sympathetic and parasympathetic systems. The PDM technique was modified for use with even a single output signal of HRV data, whereas the original. PDM required both input and output data. A detailed summary of the procedure has been presented in a previous study, and comparison to the PSD has shown that the PDM is more accurate. Detailed discussion of the PDM technique can be found in, for example, Y. Zhong et al., "Quantifying cardiac sympathetic and parasympathetic nervous activities using principal dynamic modes analysis of heart rate variability," Am. J. Physiol. Heart Circ. Physiol. 291:H1475-H1483 (2006), and Y. Zhong et al., "Nonlinear Analysis of the Separate Contributions of Autonomic Nervous Systems to Heart Rate Variability Using Principal Dynamic Modes," IEEE Transactions on Biomedical Engineering, Vol. 51, No. 2, February 2004, both of which are incorporated herein by reference in their entirety for all purposes.

A brief description of the PDM technique, as described in Y. Zhong et al., IEEE Transactions on Biomedical Engineering, Vol. 51, No. 2, February 2004, is presented herein below.

Calculation of PDMs

The estimation of PDMs using Volterra-Wiener kernels was first introduced in V. Z. Marmarelis, K. H. Chon, and D. J. Marsh, "Nonlinear analysis of renal auto-regulation in rats using principal dynamic modes," *Ann. Biomed Eng.*, vol. 27, pp. 23-31, 1999 and in V. Z. Marmarelis and M. Orme, "Modeling of neural systems by use of neuronal modes," *IEEE Trans. Biomed. Eng.*, vol. 40, pp. 1149-1158, November 1993, both of which are incorporated by reference herein in their entirety and for all purposes. The steps involved in calculation of PDMs are briefly described below. In discrete time, the general input-output relation of a stable (finite-memory) nonlinear time-invariant dynamic system is given by the discrete-time Volterra series $$y(n) = k_0 + \sum_{m=0}^{M-1} k_1(m)x(n-m) + \sum_{m_1=0}^{M-1}\sum_{m_2=0}^{M-1} k_2(m_1, m_2)x(n-m_1)x(n-m_2) + \ldots \quad (1)$$

Where $x(n)$ is the input and $y(n)$ is the output of the system. M is the memory of the system. The Volterra kernels ($k_0$, $k_1$, $k_2$, ...) describe the dynamics of the system from a hierarchy of system nonlinearities. The kernel values obtained up to a maximum lag M (kernel memory) are combined to form a real symmetric $(M+1)\times(M+1)$ square matrix (shown in (2) below) that can be used to express the second-order Volterra model response, $\hat{y}(n)$, in a quadratic form $$\hat{y}(n) = \underline{x}^T(n)Q\underline{x}(n) \quad (3)$$

where T denotes "transpose" and the (M+1)—dimensional vector $\underline{x}^T(n)=[1 x(n) x(n-1) \ldots x(n-M+1)]$ is composed of the input point epoch at each time n and a constant 1 that allows incorporation of the lower order kernel contributions in (3). Expansion of the Volterra kernels on a complete basis $\{b_j(m)\}$ transforms (1) into the multinomial expressions $$(n) = c_0 + \sum_{j=0}^{L-1} c_1(j)v_j(n) + \sum_{j_1=0}^{L-1}\sum_{j_2=0}^{L-1} c_2(j_1, j_2)v_{j_1}(n)v_{j_2}(n) + \ldots \quad (4)$$

where $$v_j(n) = \sum_{m=0}^{M-1} b_j(m)x(n-m) \quad (5)$$

and L is the number of Laguerre functions used. $\{b_j(m)\}$ are the Laguerre functions calculated with Laguerre coefficient. Thus, can be constructed with the estimated kernels $\{c_0, c_1, c_2\}$ in the following way:

$$Q = \begin{bmatrix} k_0 & \frac{1}{2}k_1(0) & \frac{1}{2}k_1(1) & \ldots & \frac{1}{2}k_1(M-1) \\ \frac{1}{2}k_1(0) & k_2(0,0) & k_2(0,1) & \ldots & k_2(0, M-1) \\ \frac{1}{2}k_1(1) & k_2(1,0) & k_2(1,1) & \ldots & k_2(1, M-1) \\ \vdots & \vdots & \vdots & \ddots & \vdots \\ \frac{1}{2}k_1(M-1) & k_2(M-1,0) & k_2(M-1,1) & \ldots & k_2(M-1, M-1) \end{bmatrix} \quad (2)$$

$$Q = \begin{bmatrix} c_0 & \frac{1}{2}c_1^T B^T \\ \frac{1}{2}Bc_1 & B^T c_2 B \end{bmatrix} \quad (6)$$

where $B = [b_0^T \; b_1^T \; \ldots \; b_{L-1}^T]$.

Laguerre functions are chosen as an appropriate orthonormal basis because they exhibit exponential decaying properties that make them suitable for physiological systems modeling. In addition, due to basis function expansion, the estimation accuracy is maintained even with a small data length. It has been previously shown that a data length of 250 points is sufficient for accurate kernel estimation using Laguerre expansions.

Since Q is a real symmetric square matrix, it can always be decomposed in the following way:

$Q=R\Lambda R^T$ where the eigenvector matrix R will always be an orthonormal matrix. $\Lambda$ is the diagonal eigenvalue matrix. The significant eigenvalues are selected from $\Lambda$ and the corresponding orthonormal eigenvectors define the PDMs of this system. For each significant $\lambda_s$, eigenvalue, the values of the corresponding eigenvector $\underline{\mu}_s^T = [\mu_{s,0} \; \mu_{s,1} \ldots \mu_{s,M}]$ (with the exception $\mu_{s,0}$ of) define the sth PDM $$p_s(m) = [\mu_{s,1} \; \mu_{s,2} \ldots \mu_{s,M}]. \quad (7)$$

The obtained s th PDM generates the Sth mode via convolution with the input $x(n)$. The second-order model estimation $\hat{y}$ using S PDMs is $$\hat{y}(n) = \sum_{s=1}^{S} \lambda_s \{p_s(m) * x(n)\} + \mu_{s,0})^2. \quad (8)$$

The nonzero values $\{\mu_{s,0}\}$ give rise to the contribution of linear terms.

Detrending Method

The detrending method that was utilized is based on smoothness priors approach and operates like a time-varying FIR filter. The Matlab source code as provided in M. Tarvainen, P. Ranta-Aho, and P. Karjalainen, "An advanced detrending method with application to HRV analysis," *IEEE Trans. Biomed. Eng.*, vol. 49, pp. 172-175, February 2002, which is incorporated by reference herein in its entirety and for all purposes, for applying the detrending method to a signal, Y, is as follows:

$T$=length($Y$);

lambda=500;

$I$=speye($T$);

$D2$=spdiags(ones($T$-2,1)*[1-21],[0:2],$T$-2,$T$);

result=($I$-inv($I$+lambda^2*$D2$'*$D2$))*$Y$.

The lambda controls the degree of detrend desired. For the analysis in Y. Zhong et al., IEEE Transactions on Biomedical Engineering, Vol. 51, No. 2, February 2004, the value of lambda was adjusted so that the mean power of the VLF was dose to the mean power of the LF and HF without affecting the power in the LF. The value of lambda differed for each subject with the range of values varying from 500 to 10 000.

In another instance, the above described method, implemented in a computing device, a portable communication device in one instance, as used in processing the collected data includes detrending the collected data to obtain output data, delay the detrended data by one unit to obtain input data, forming a principal matrix using Volterra kernels based on the input and the output, and eigendecomposing the principal matrix using a predetermined number of orthonormal functions as a basis to obtain eigenvalues and eigenvectors of the principal matrix. The primary and secondary components respectively correspond to two of the eigenvectors associated with the first two greatest eigenvalues of the principal matrix. The orthonormal functions comprise Laguerre functions.

In yet another instance, processing of the input data includes obtaining a fit to the collected data using the time varying optimal parameters search (TVOPS) algorithm (the TVOPS algorithm is described in Rui Zou, Hengliang Wang, and Ki H. Chon, A Robust Time-Varying Identification Algorithm Using Basis Functions, *Annals of Biomedical Engineering*, Vol. 31, pp. 840-853, 2003, which is incorporated by reference herein in its entirety and for all purposes), obtaining a residual using the fitted data and the collected data, and applying the PDM algorithm with the collected data as the output signal and the residual as the input signal. From the result of the PDM algorithm the primary and secondary components are obtained.

While the PDM is a time-domain representation, it may be converted to the frequency domain via the Fast Fourier Transform (FFT). This facilitates validation of the two ANS activities, as they are usually illustrated in the frequency domain. Therefore, hereafter, the PDM's dynamic characteristics are described in the frequency domain. In this particular embodiment, 8 Laguerre functions are used with a memory length of 60. The calculation of PDMs and the choice of Laguerre functions and memory lengths may vary depending on design preferences. The derived. PDM's two main dynamics are referred to here as the sympathetic and parasympathetic.

Cases C-E: Western Blot Analysis

As shown in Table 1, thirty male 2-, 3-, and 4-month old wild-type C57BL/6 (n=5 for each age) and Akita (n=5 for each age) mice are studied to quantify the development of nerve degeneration by Western blotting. The atrial section of the heart is used for Western blotting of heart tissue since autonomic nerves are more prevalent in the sinoatrial and atrial ventricular nodes. The atrial tissues are homogenized, the proteins fractionated according to size by SDS-PAGE, and then transferred onto a membrane for probing with specific antibodies. In this particular embodiment, three autonomic nerve protein markers are used: tyrosine hydroxylase (TH), a marker for sympathetic nerves (anti-TH, ab112, Abcam Inc. (1:200 dilution)); choline acetyltransferase (ChAT), a marker for parasympathetic nerves (anti-Choline acetyltransferase, AB144P, Millipore Inc. (1:200 dilution)); and synaptophysin (SYN), a non-selective marker for nerves (anti-SYN, sc-9116, Santa Cruz Biotechnology, Inc. (1:500 dilution)). Actin (anti-actin, ab50412, Abcam, Inc. (1:5,000 dilution)) is used as a loading volume control. The secondary antibody comprises anti-rabbit horseradish peroxidase antibody from goat, A6154, Sigma-Aldrich (1:10,000 dilution).

To quantitatively compare protein density in C57BL/6 and Akita mice, the integrated density of each protein expression bar is recorded and compared after normalization to actin density in each column.

Tissue Collection for Western Blot

Age-matched wild-type C57BL/6 and Akita mice are euthanized in a $CO_2$ chamber. The heart is rapidly excised, and placed into ice-cold phosphate buffered saline (PBS). The atria is separated from the ventricles and washed in clean ice-cold PBS three times each to remove any blood. Any connective tissue attached to the atria is scraped off. The tissues are then moved into a microcentrifuge tube, snap frozen with liquid nitrogen, and stored at $-80°$ C.

Tissue Preparation for Western Blot

After thawing the frozen atrial tissue samples on ice, they are placed into RIPA Buffer (1 mL, R0278, Sigma-Aldrich), Protease Inhibitor Cocktail (100 µL, P2714, Sigma-Aldrich), PMSF (10 µL), and Sodium Orthovanadate (20 µL) (a total volume of 350 µL is added to each tissue sample). The tissue is diced with a scalpel and kept on ice for 1 hour (with periodic vortexing). After lysis, the samples are centrifuged at 14,000 rpm for 5-8 minutes at 4° C. The supernatant are then transferred to a new sterile tube and frozen at $-80°$ C.

SDS Polyacrylamide Gel Electrophoresis and Protein Transfer for Western Blot

Thirty micrograms of protein from each sample is diluted with Laemmli Sample Buffer (Bio-Rad) (1:1 dilution), heated at 95° C. for 5 minutes, and then centrifuged at 14,000 rpm for 1 minute. The samples are loaded onto a freshly prepared 10% SDS polyacrylamide gels adjacent to 5 µL of a protein ladder standard (PageRuler, Fermentas). Electrophoresis is performed at a constant 115 V (~25 mA) in an electrophoresis running buffer (25 mM Tris, 192 mM Glycine, and 0.1% SDS) until the dye front reached the bottom of the gel (~1 hour). At this point, the gel is removed from the gel apparatus and rinsed with 1×TBS-T, Protein is transferred to a PVDF membrane by transverse electrophoresis in a Genie Blotter (Research Products International) as described by the manufacturer using 25 mM Tris, 192 mM Glycine, and 20% Methanol as the transfer buffer and 100 V for 1 hour at 4° C. After the transfer, the PVDF membrane is removed from the apparatus and washed with 1×TBS-T.

General Immunoblotting Procedure for Western Blot

The membrane is first placed into a blocking solution (5% Bio-Rad Blotting Grade Blocker non-fat dry milk, in 1×TBS-T) for 1 hour at room temperature. Next, the membrane is placed in 1% blocking solution containing the primary antibody overnight at 4° C. The membrane is then washed 6 times for 1.5 minutes each with 1×TBS-T. Afterwards, the membrane is placed into 1% blocking solution containing secondary antibody for 1 hour at room temperature, then washed again 6 times for 15 minutes each with 1×TBS-T.

Membrane Stripping for Western Blot

Probed membranes are placed into a stripping buffer (62.5 mM Tris-HCL, 2% SDS, and 100 mM β-mercaptoethanol) at 50° C. for 30 minutes, then washed 6 times for 5 minutes each with 1×TBS-T. The membrane may then be re-probed following the above protocol.

Imaging for Western Blot

Chemiluminescence solution (Amersham ECL™ Western Blotting Analysis System, RPN2109, GE Healthcare) is mixed immediately before imaging. The PVDF membrane is soaked in the mixed solution for 1 minute prior to camera exposure. The image of the membrane is obtained by exposure to a Chemi Doc camera for 5 minutes. The ladder image and blotting image are exposed separately and overlaid in Photoshop afterwards.

Case F: Immunohistochemistry Analysis

Similar to the Western blot analysis, immunohistochemical analysis of autonomic innervation in the heart (near either the sinoatrial (SA) node or the atrioventricular (AV) node) involved the generic nerve marker synaptophysin (SYN). The heart is snap frozen at $-80$ C. immediately after being excised from the animal and sections around the SA node area are obtained and fixed on Super Frost Slides. The slides are prepared by sectioning the tissue into 6 micrometer thick slices. The sections are fixed in paraformaldehyde and then stained with SYN as well as with an HCN4 antibody. HCN4 is a channel protein only found in the SA node, and therefore, it is used as a location control for the SA node. The stained cardiac sections are examined on a Zeiss confocal microscope, and the SA and AV nodes are assessed to quantify sympathetic and parasympathetic innervation. It is well known that the SA and AV nodes are densely innervated by the autonomic nerves. All samples for each mouse are from the same block and the images are subjected to overall contrast enhancement. The overall nerve density expression is investigated using synaptophysin; HCN4, a membrane channel found only in SA and AV nodes in the heart, is used to ensure that the excised atrial tissue section is correctly localized since the autonomic nerves are most abundant in these nodes.

Statistical Analysis of HRV Methods and Western Blot Results

For each week's HRV analysis, Student's t-test is applied to test the difference between Akita and wild-type mice, followed by the Jarque-Bera normality test. One-way analysis of variance (ANOVA) with repeated measurement is used to test any significant difference between all weeks. Data from two other independent data segments are also tested using one-way ANOVA. The null hypothesis is rejected when the p-value<0.05, All statistics may be performed using SigmaStat 3.0 (SPSS Inc., Chicago, Ill.) and Matlab (The Mathworks, Natick, Mass.).

For each Western blot comparison, the image is inverted and the integrated density of each relevant protein band is recorded (using Adobe Photoshop CS4, Adobe). This density value is divided by the integrated density value of actin band in the same lane to obtain a normalized value. Student's t-test is also applied to test the normalized integrated density value between Akita and wild-type mice, followed by the Jarque-Bera normality test. The null hypothesis is rejected when the p-value<0.05.

Results

Time and Frequency Parameters from HRV Analysis of Case A (4-Month Old Mice at Start; Telemetry Recordings)

One may choose three randomly-selected daily 15 minute segments that are deemed to be in a quiet state as determined by the activity data. It is found that no significant difference in time- and frequency-domain parameters between the three quiet state segments. Thus, results from one arbitrary 15 minute data segment from a quiet state may be presented. Comparisons of the traditional HRV time and frequency domain measures to PDM analysis are provided in below Table 3 for both strains of mice. As shown in Table 3, mean HR is significantly depressed in Akita mice for all four weeks. SDN is also significantly lower in Akita mice in weeks 3 and 4. However, RMSSD increases in Akita mice in weeks 3 and 4.

TABLE 3

Comparison of Different Methods for HRV Analysis Derived from ECG

| | | Week 1 | Week 2 | Week 3 | Week 4 |
|---|---|---|---|---|---|
| HR | Wild-type | 505 ± 35 | 531 ± 21 | 549 ± 31 | 530 ± 19 |
| | Akita | 421 ± 56* | 417 ± 66* | 396 ± 36* | 375 ± 26* |
| SDNN | Wild-type | 8.25 ± 1.13 | 7.96 ± 1.12 | 8.78 ± 1.61 | 8.34 ± 1.26 |
| | Akita | 6.31 ± 1.94 | 6.37 ± 0.96 | 6.26 ± 1.01* | 5.88 ± 1.18* |
| RMSSD | Wild-type | 1.66 ± 0.73 | 1.73 ± 0.39 | 1.81 ± 0.29 | 1.94 ± 0.38 |
| | Akita | 1.69 ± 0.64 | 2.01 ± 0.77 | 2.24 ± 0.21* | 2.28 ± 0.30* |
| PSD LF | Wild-type | 3.48 ± 0.18 | 3.61 ± 0.11 | 3.62 ± 0.21 | 3.55 ± 0.22 |
| | Akita | 2.97 ± 0.26* | 3.07 ± 0.40* | 2.93 ± 0.34* | 3.05 ± 0.13* |
| PSD HF | Wild-type | 0.73 ± 0.14 | 0.69 ± 0.14 | 0.73 ± 0.12 | 0.76 ± 0.08 |
| | Akita | 0.77 ± 0.08 | 0.92 ± 0.18* | 0.99 ± 0.09* | 0.97 ± 0.11* |
| LF/HF | Wild-type | 5.99 ± 0.95 | 6.49 ± 0.55 | 6.74 ± 1.35 | 6.12 ± 0.54 |
| | Akita | 5.76 ± 0.77 | 5.15 ± 2.5 | 4.43 ± 0.80* | 4.73 ± 0.39* |
| PDM Symp. | Wild-type | 0.86 ± 0.04 | 0.86 ± 0.04 | 0.90 ± 0.06 | 0.88 ± 0.03 |
| | Akita | 0.76 ± 0.06* | 0.77 ± 0.07* | 0.72 ± 0.05* | 0.72 ± 0.06* |
| PDM Para. | Wild-type | 5.04 ± 0.49 | 5.27 ± 0.51 | 5.07 ± 0.42 | 4.89 ± 0.35 |
| | Akita | 4.26 ± 0.34* | 4.19 ± 0.62* | 4.38 ± 0.41* | 4.27 ± 0.30* |
| Symp. Para. | Wild-type | 0.21 ± 0.01 | 0.22 ± 0.03 | 0.23 ± 0.04 | 0.24 ± 0.02 |
| | Akita | 0.18 ± 0.02* | 0.19 ± 0.02* | 0.19 ± 0.01* | 0.18 ± 0.03* |

Mean ± STD,
*denotes statistical significance from Akita to wild-type ($p < 0.05$)

The LF power of Akita mice is consistently lower than wild-type mice throughout the entire month. However, the HF power is significantly higher in Akita mice as compared to wild-type mice in weeks 2-4. Therefore, the LF/HF ratio is significantly lower in Akita mice as compared to wild-type mice in weeks 3-4. However, when these values are compared amongst each week in Akita mice, there is no difference suggesting that progressive changes in these parameters did not occur. The same observations are found for the two other data segments (not shown) suggesting that the results are consistent and are not based on the choice of which data segments are selected from the day-long data record.

PDM Analysis of HRV

As shown in Table 3, both sympathetic and parasympathetic dynamics for all four weeks are found to be significantly reduced in Akita mice. Note that the decrease in parasympathetic dynamics in Akita mice using the PDM method is in contrast to the PSD and RMSSD results. Moreover, the Sympathetic/Parasympathetic ratio decreases significantly which is indicative of the autonomic imbalance in diabetic mice. A progressive degradation of the autonomic nervous activities over time (e.g., from week 1 to 4) is not observed. Further, there is no difference in the PDM parameters among the three different data segments (not shown).

Time and Frequency Parameters from HRV Analysis of Case B (1.5-Month Old Mice at Start; Pulse Oximeter Recordings)

Figure 1B:
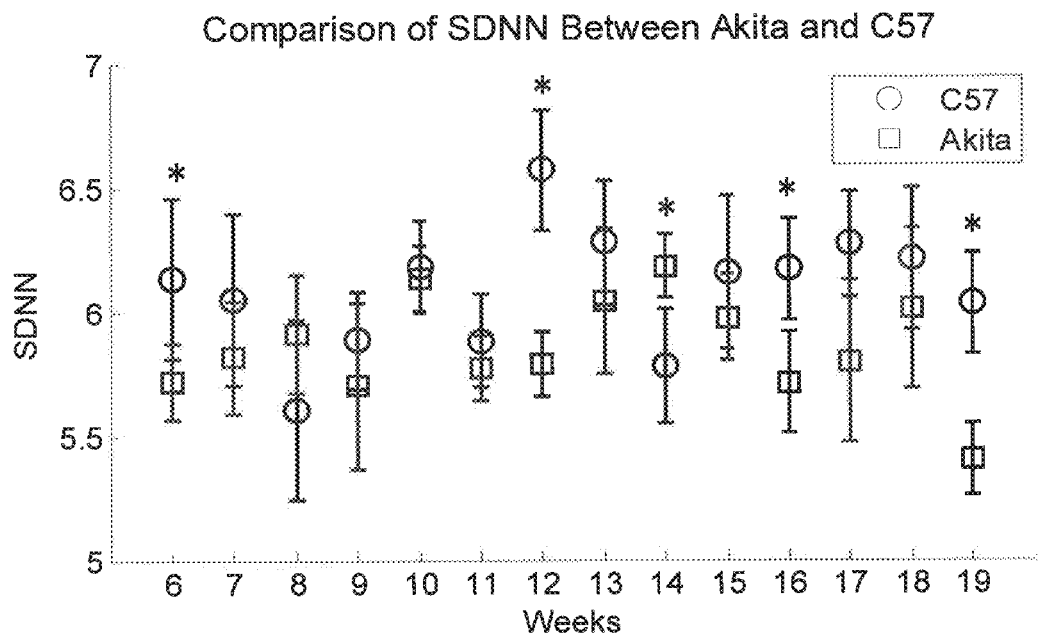
FIG. 1B illustrates the comparison of SDNN between Akita and wild-type mice, the data being recorded from a pulse oximeter.
Figure 1C:
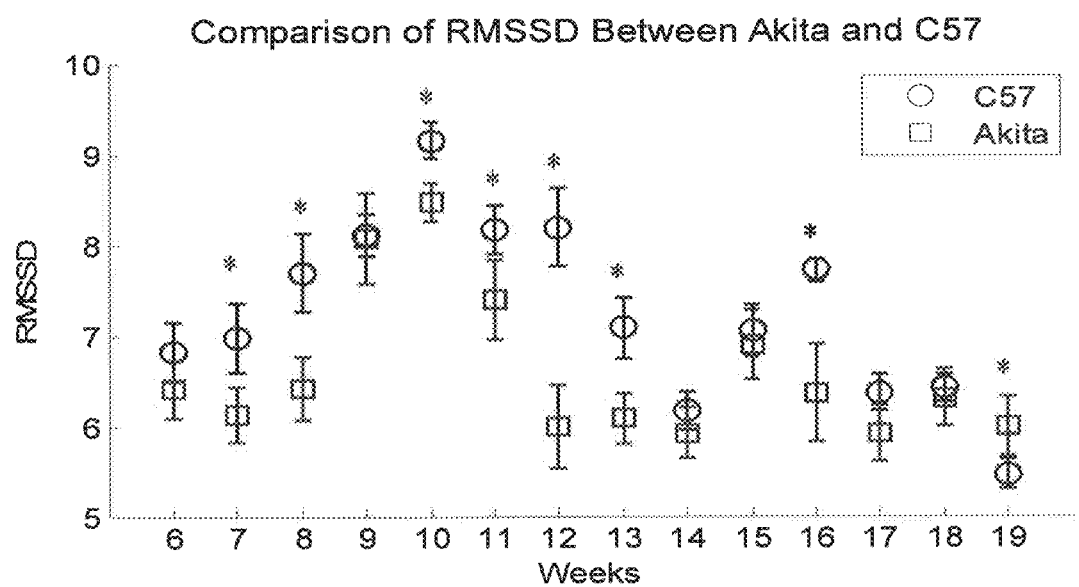
FIG. 1C illustrates the comparison of RMSSD between Akita and wild-type mice, the data being recorded from a pulse oximeter.

The standard time- and frequency-domain parameters are investigated on a weekly basis. Results are recorded from week 6 through week 19, thus, 14 weeks of data comparison are presented. Each data point is the average of each week, which consists of 15 minutes per day for 5 days per week. It is found that a consistently and significantly decreased mean heart rate in Akita mice starting at week 9, as shown in FIG. 1A. The SDNN values decrease significantly in Akita mice in some weeks ($12^{th}$, $16^{th}$ and $19^{th}$ week) but not in others, and increased in week 14, as shown in FIG. 1B. The RMSSD, on the other hand, showed a significant decrease in week 12, no difference in week 16 and a significant increase in week 19, as shown in FIG. 1C.

Figure 2A:
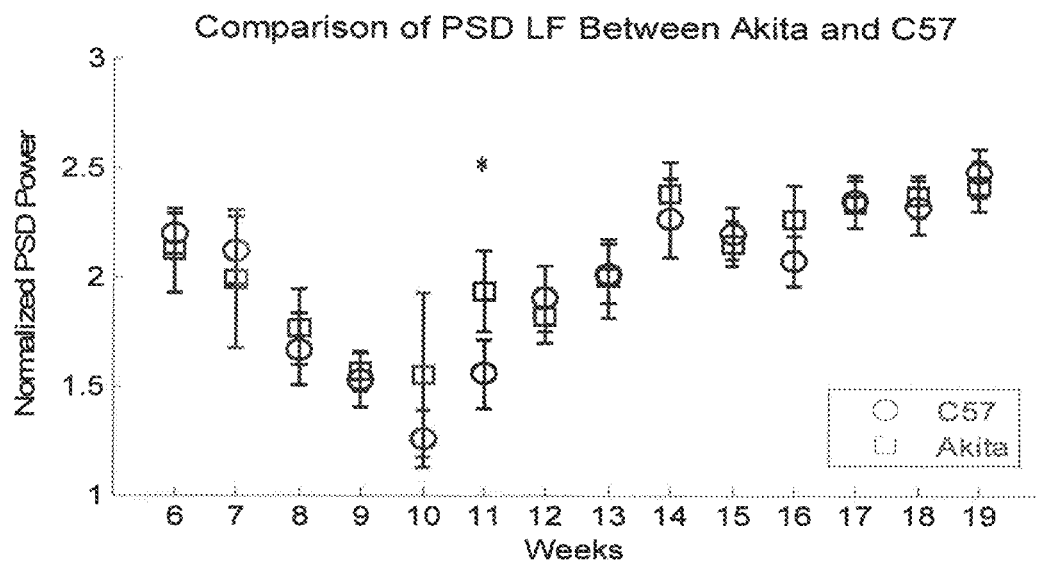
FIG. 2A illustrates the comparison of low frequency between Akita and wild-type mice, the data being recorded from a pulse oximeter.
Figure 2B:
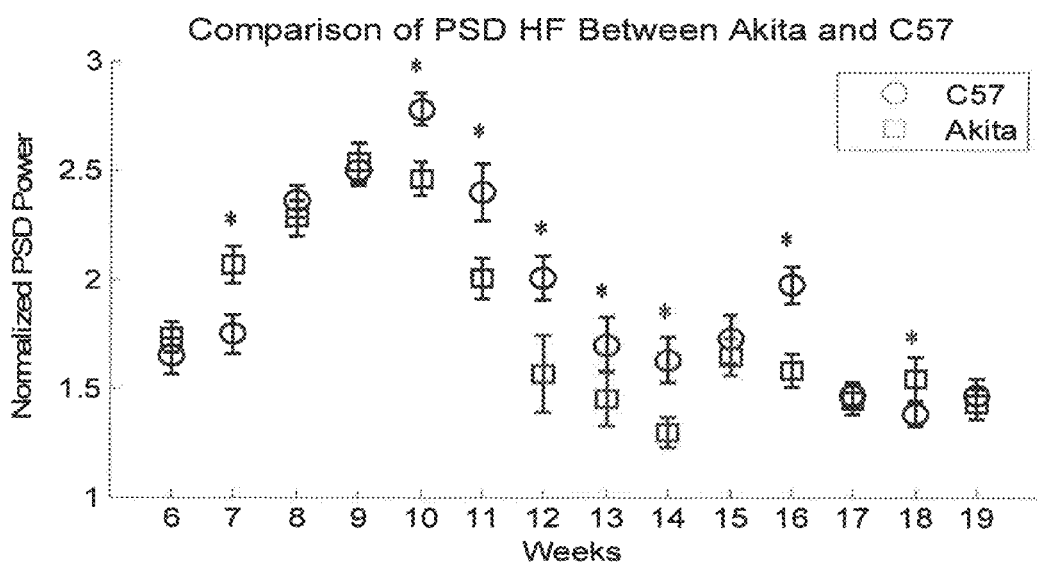
FIG. 2B illustrates the comparison of high frequency between Akita and wild-type mice, the data being recorded from a pulse oximeter.
Figure 2C:
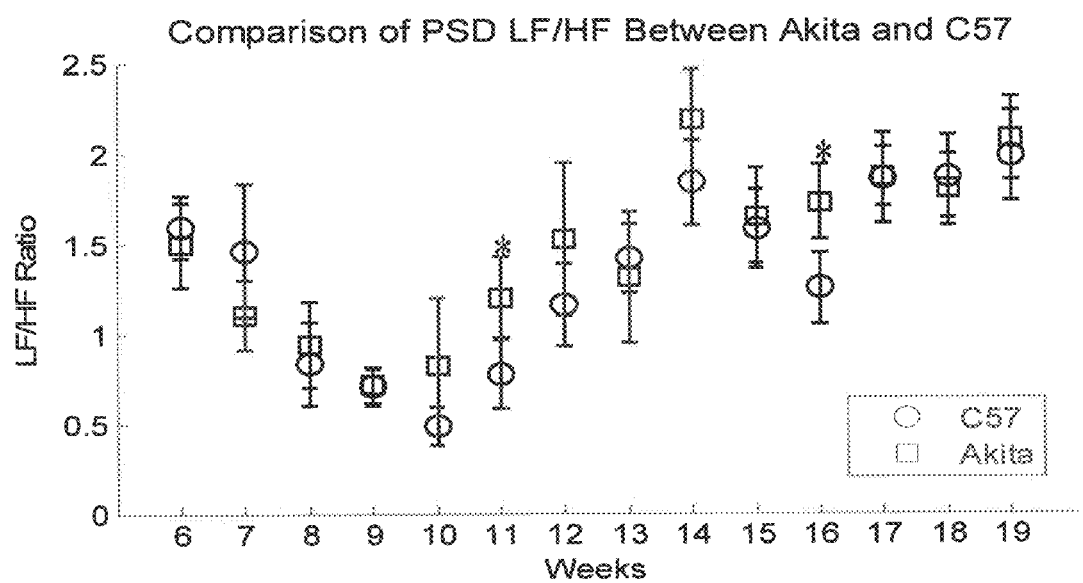
FIG. 2C illustrates the comparison of LF/HF between Akita and wild-type mice, the data being recorded from a pulse oximeter.

As shown in FIG. 2A, no significant change in the normalized LF power is observed in Akita mice throughout the experiment (except for week 11). As shown in FIG. 2B, the HF power does not change initially in Akita but a significant reduction in weeks 10 to 14 and also week 16 is noted; on week 18, HF power is increased in Akita. Consequently, as shown in FIG. 2C, the LF/HF ratio shows similar patterns as those of LF and HF powers in that some weeks when there is significant decrease, whereas in other weeks there is either no difference or significant increase. Similar to RMSSD and SDNN values, the frequency domain parameters between the two strains are not consistent throughout the experiment.

Figure 3A:
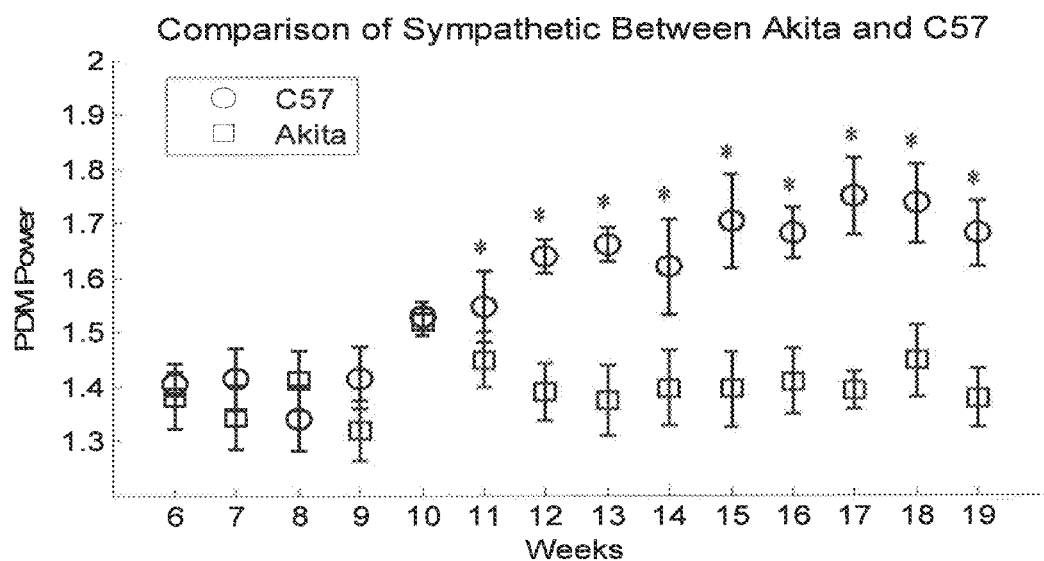
FIG. 3A illustrates the comparison of sympathetic between Akita and wild-type mice, the data being recorded from a pulse oximeter and the analysis being done by PDM.
Figure 3B:
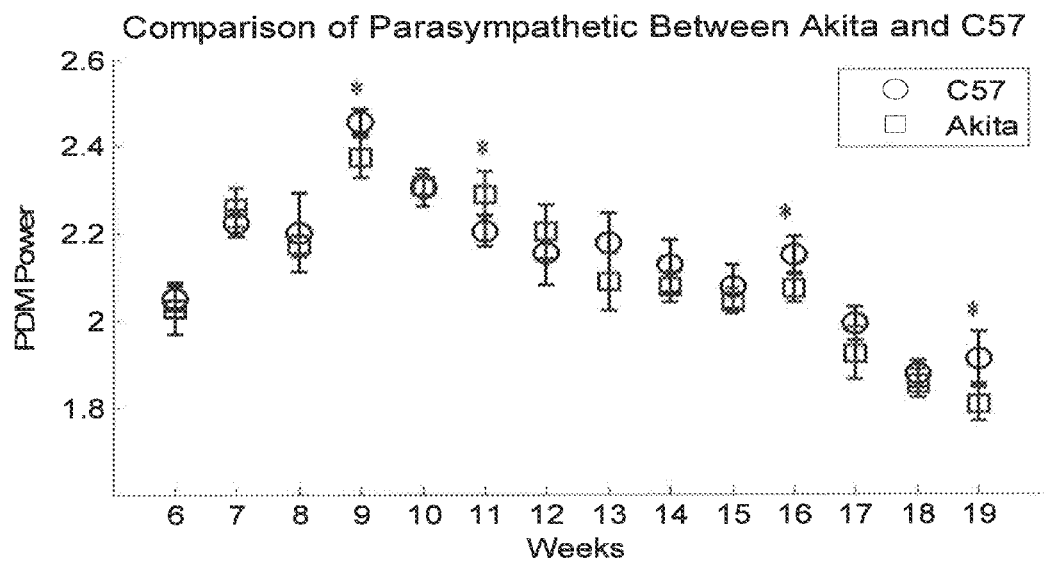
FIG. 3B illustrates the comparison of parasympathetic between Akita and wild-type mice, the data being recorded from a pulse oximeter and the analysis being done by PDM.
Figure 3C:
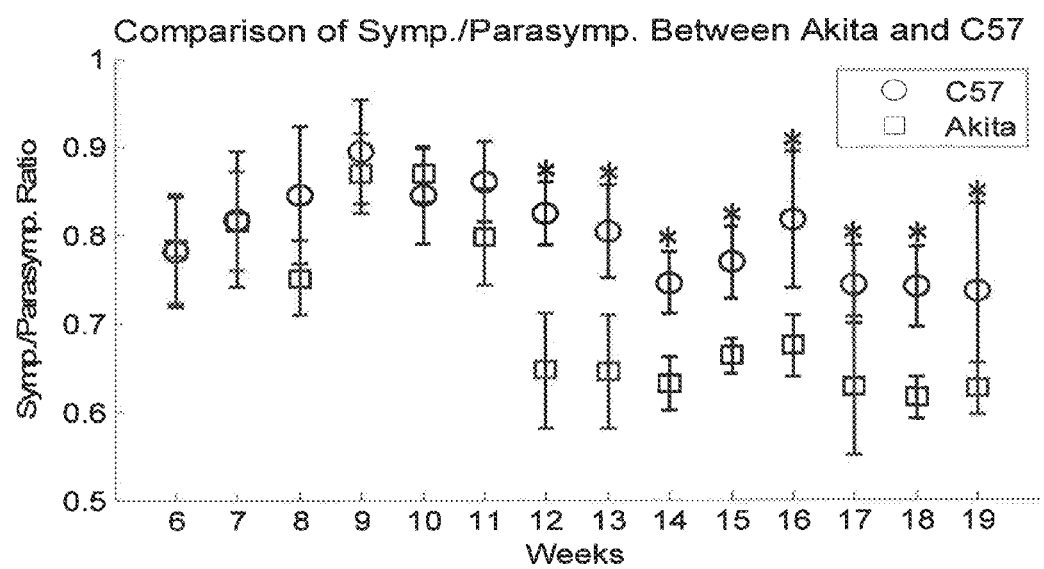
FIG. 3C illustrates the comparison of symp/parasymp ratio between Akita and wild-type mice, the data being recorded from a pulse oximeter and the analysis being done by PDM.

As shown in FIG. 3A, the PDM-derived sympathetic power remains unchanged initially and then decreases from week 11-19 in Akita mice. This result suggests that depressed or impaired sympathetic activities are present as early as 3 months in Akita mice and become more severe as they age. In contrast, as shown in FIG. 3B, the parasympathetic power via VDM shows no significant change for most time points between the two strains. Note that data are recorded in an active state where parasympathetic activity is suppressed. Thus, differences between the parasympathetic activities of Akita and C57 are not likely to be detectable. As shown in FIG. 3C, the Sympathetic/Parasympathetic ratio is found to be significantly lower with Akita than wild-type mice starting at week 12 and continuing to the end of the experiment.

Cases C-E: Western Blot Assessment of Autonomic Nerve Density

Figure 4A:
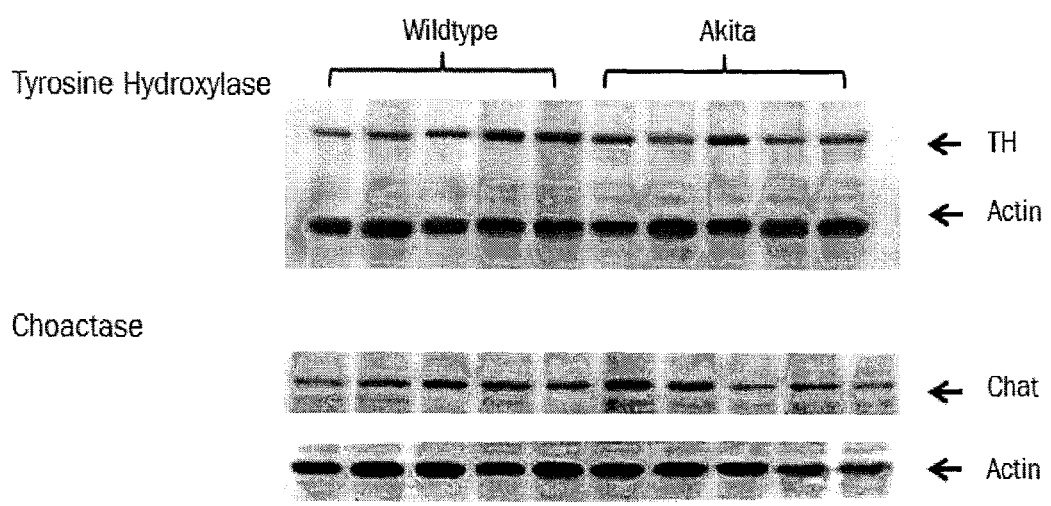
FIG. 4A illustrates Western blot analysis of heart tissue extracts from Akita (n=5) versus wild-type (n=5) mice at 4 months of age. Where SYN is a general nerve protein marker, Chat is a marker of the parasympathetic nerves, and TH is a marker of the sympathetic nerves.

It appears that only the PDM approach may indicate consistently significantly reduced autonomic activity in Akita mice when compared to C57/Bl6 mice, Western blotting is performed to determine whether the autonomic nervous function data obtained by the PDM method correlates with nerve rarefaction in the SA and AV nodes in both strains of mice. As shown in FIG. 4A, the autonomic nerve protein markers SYN, TH, and ChAT are all significantly less abundant in the 4 month old Akita than the age-matched wild-type mice (see below Table 4).

Figure 4B:
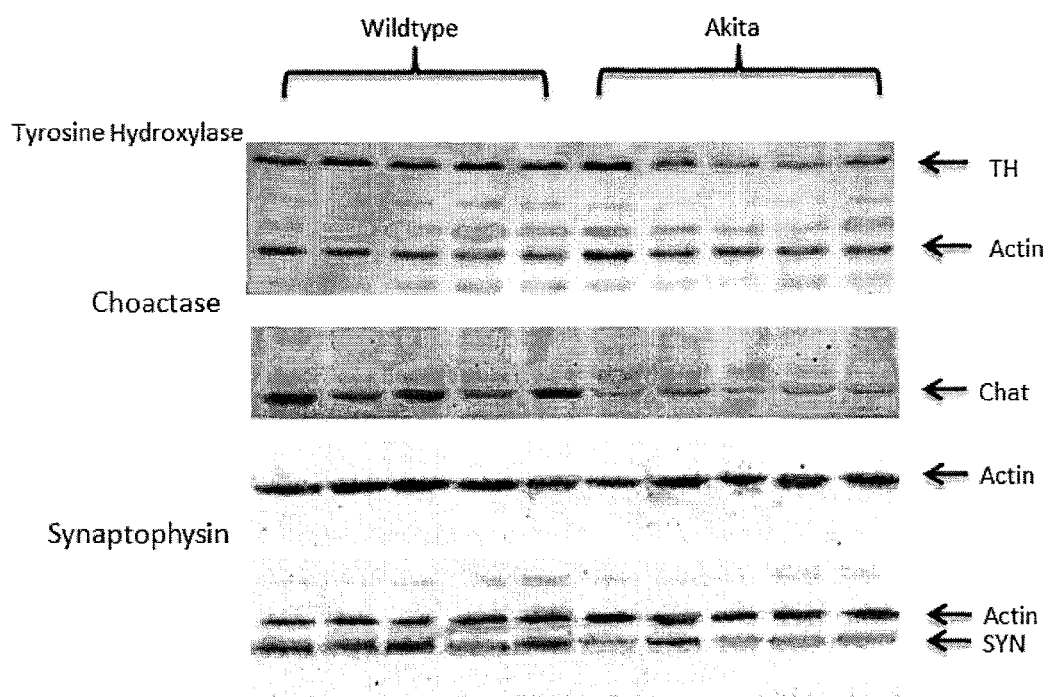
FIG. 4B illustrates Western blot analysis of heart tissue extracts from Akita (n=5) versus wild-type (n=5) mice at 3 months of age, where SYN is a general nerve protein marker, Chat is a marker of the parasympathetic nerves, and TH is a marker of the sympathetic nerves.
Figure 4C:
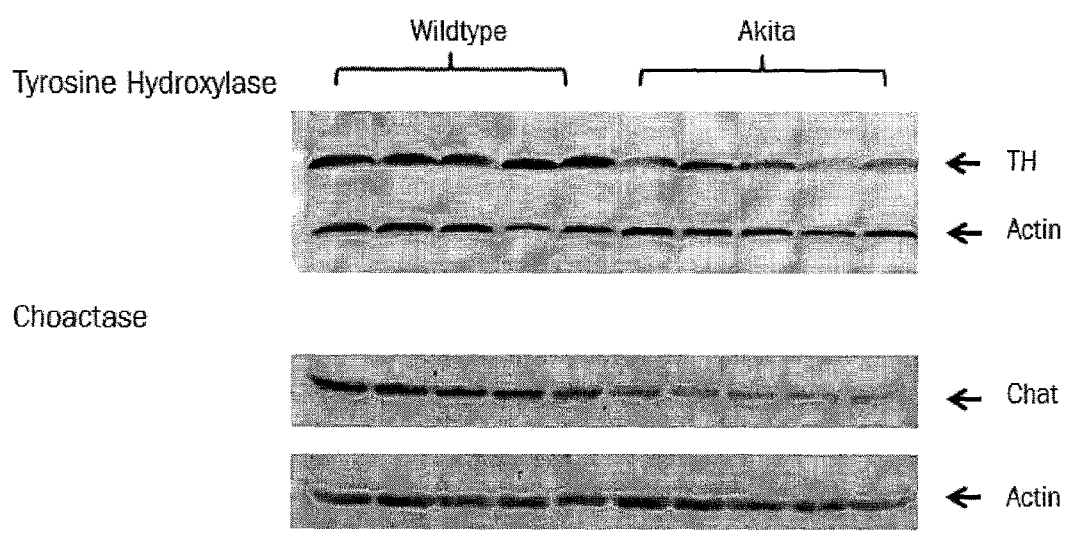
FIG. 4C illustrates Western blot analysis of heart tissue extracts from Akita (n=5) versus wild-type (n=5) mice at 2 months of age, where SYN is a general nerve protein marker, Chat is a marker of the parasympathetic nerves, and TH is a marker of the sympathetic nerves.

The possibility of autonomic nerve rarefaction in younger (3-month old) Akita and age-matched wild-type mice is also investigated. FIG. 4B shows Western blot of TH, SYN, and ChAT antibodies in 3-month old mice (Akita n=5 and wild-type n=5). After normalizing the integrated density to actin, a significant reduction is found in Akita mice. The same experiments may be performed on 2-month old mice (FIG. 4C, Akita n=5 and wild-type n=5). There is no significant reduction in abundance of any of the three proteins at 2 months. These results are summarized in below Table 4.

TABLE 4

Quantification of Western Blot Analysis

| | | TH | Chat | SYN |
|---|---|---|---|---|
| 4 months | Wild-type | 1.52 ± 0.18 | 0.99 ± 0.27 | 1.14 ± 0.43 |
| | Akita | 1.18 ± 0.20* | 0.66 ± 0.13* | 0.50 ± 0.15* |
| 3 months | Wild-type | 1.11 ± 0.12 | 1.06 ± 0.07 | |
| | Akita | 0.87 ± 0.15* | 0.84 ± 0.02* | |
| 2 months | Wild-type | 0.48 ± 0.08 | 0.65 ± 0.12 | |
| | Akita | 0.49 ± 0.05 | 0.62 ± 0.07 | |

Figure 5:
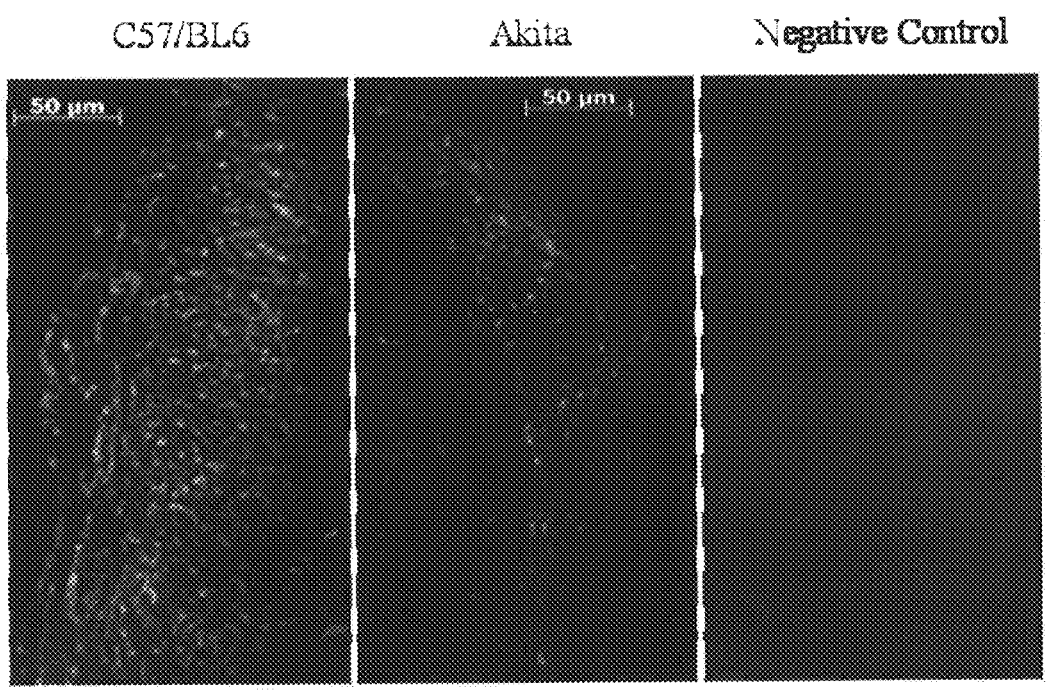
FIG. 5 illustrates representative images of immunostained heart tissue sections from wild-type and Akita mice, where HCN4 immunostaining (red fluorescence) indicates that these sections are from the SA node region of the mouse heart, and SYN (green fluorescence) is a marker for nerves.

*denotes statistical significance with $p < 0.05$, Wild-type: n = 5 and Akita: n = 5 for each age group Case F: Immunohistochemistry of Cardiac Autonomic Nerves The immunohistochemical analysis is performed on 4 month old mice to examine if indeed SYN expression is reduced in Akita mice. FIG. 5 shows a stack of deconvolved optical sections of the immunostaining of SA nodes for HCN4 (red) and SYN (green). The negative control is obtained by omitting both primary antibodies and the image is not deconvolved. The tissue sections are stained concurrently and imaged with the same settings. As shown in FIG. 5, the SA node in this Akita mouse is clearly less densely innervated than that of the C57BL/6 control mouse.

Figure 6:
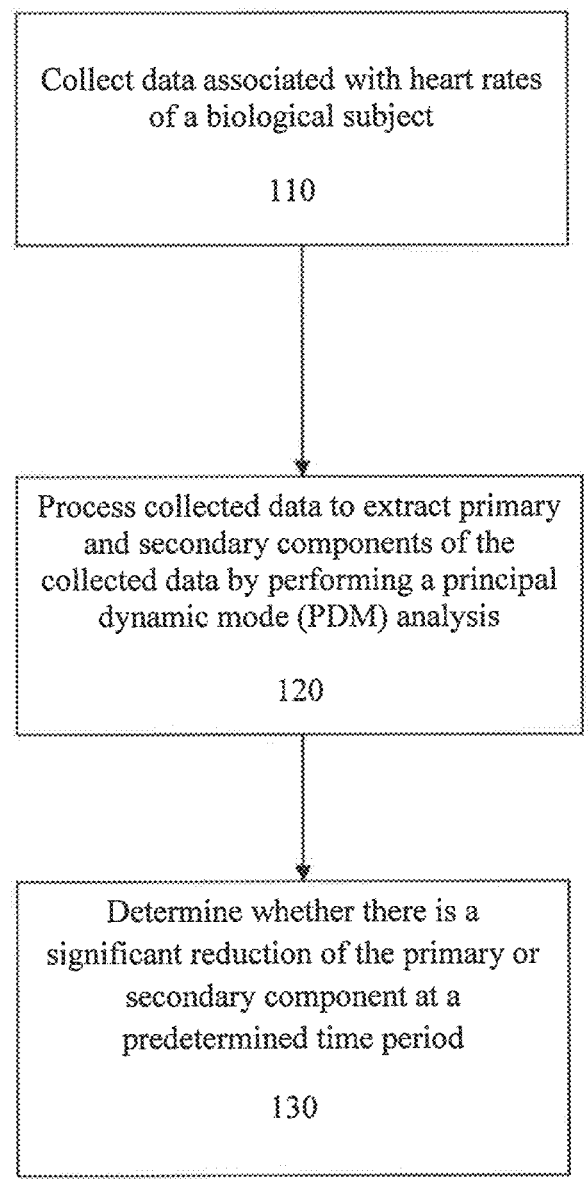
FIG. 6 is a flowchart of one embodiment of the method of these teachings.

FIG. 6 is a flowchart of one embodiment of the method of these teachings, as described herein above. Referring to FIG. 6, in the embodiment shown therein, the data associated with heart rates of the biological subject is collected (step 110, FIG. 6). A principal dynamic mode (PDM) analysis is performed on the collected data and primary and secondary components are extracted (step 120, FIG. 6). A determination is made as to whether there is a significant reduction in the primary or secondary components over a predetermined time, for example, as in Table 3 (step 130, FIG. 6). The significant reduction of the primary or secondary component at the predetermined time period is indicative of the DCAN development.

Discussion

An alternative to the power spectral density approach has been illustrated, which is termed principal dynamic mode (PDM) analysis, to estimate the dynamics of the autonomic nervous system from heart rate fluctuation data. Unlike the PSD, the PDM method provides separation of the dynamics associated with the parasympathetic and sympathetic nervous systems. The advantages of using the PDM method over the traditional HRV measures have already been demonstrated in a previous study involving healthy subjects with the aid of pharmacological blockade, and in swine exposed to neurological decompression sickness which resulted in severe impairment of the autonomic nervous system.

Estimates of the ANS dynamics derived via the PDM from the ECG recordings (Case A in Table 1) are found to correlate with levels of autonomic nerve markers measured by Western blot analysis. However, the traditional HRV approaches to estimate the autonomic nervous system's dynamics based on either the time domain or power spectral density parameters does not correlate with the Western blot results. Specifically, the Western blot results show parasympathetic nerve rarefaction in 4-month old Akita mice, but both HF power and RMSSD values (see Table 3) shows a significant increase in the parasympathetic tone. In contrast, the PDM shows a significant decrease in the parasympathetic dynamics. Immunohistochernical staining and Western blot analysis of heart tissue samples shows a significant decrease in both the parasympathetic and sympathetic activities or innervation in the 4-month old Akita mice as compared to wild-type mice, which is in agreement with the results from the PDM, but not the PSD or time-domain measures.

Similarly, the results obtained from the PSD and the traditional time-domain HRV measures derived from the PPG (pulse oximeter) recordings (Case B) do not correlate with the reduction in nerve marker proteins observed in Akita mouse heart tissue by Western blot analysis. In particular, the Western blot results indicates that nerve rarefaction in Akita mice started at 3 months and persisted as they aged, but the PSD and time-domain measures do not show such differences in autonomic nervous system dynamics between the wild-type and Akita mice for all time durations. The PDM, consistent with the Western blot analysis, shows depressed sympathetic dynamics and autonomic imbalance starting at 3 months. The parasympathetic dynamics derived from the PDM, however, does not show consistent nerve rarefaction in Akita mice when compared to wild-type at either 3 or 4 months. Without wishing to be bound by theory, it is believed that this is due to the fact that PPG recordings (Case B in Table 1) are made during an active state which is dominated by the sympathetic and depressed parasympathetic nervous dynamics. Hence, the parasympathetic difference between Akita mice and wild-type mice is likely to be minimal during the active state. For the quiet state data (Case A in Table 1), a decrease in the parasympathetic dynamics in Akita mice can be discerned, partly because parasympathetic dynamics are accentuated, hence, any difference between wild-type and Akita mice can be magnified. The depressed parasympathetic dynamics seen in 4-month old Akita mice with ECG but not with PPG recordings does not appear to be due to the different measuring devices. This is because previous works have shown that accurate heart rate fluctuation data can be obtained from PPG recordings.

The 4-month old Akita mice are studied because peripheral neuropathy is known to occur after mice have reached this age. Results in the present disclosure suggest that DCAN is also present in 4-month old Akita mice. These results are in agreement with ECG-telemetry studies involving adult rats treated with streptozotocin (STZ) which led to development of diabetes with significant reductions in both heart rate and HRV, including reductions in power spectral density at higher frequencies, suggesting that the parasympathetic drive to the heart may be altered during the early stages of STZ-induced diabetes. Longer duration telemetric recordings (e.g., 22 weeks) assessing the effect on rats of STZ-induced diabetes demonstrate similarly altered autonomic activities (both sympathetic and parasympathetic) commencing at 4 weeks followed by similarly continuous depressed autonomic activities even up to a duration of 22 weeks. Insulin treatment of these STZ-treated diabetic rats shows no significant recovery of the autonomic nervous activity even though heart rate recovers to the pre-STZ treated state. This suggests that heart rate itself is not a reliable diagnostic marker of DCAN. The literature on diabetic complications subsequently leading to DCAN symptoms in mice is sparse, however.

Given that DCAN occurs in 4-month old Akita mice, one may be interested in knowing if DCAN occurs prior to 4 months. To examine DCAN onset in mice as early as 1.5 months, a tail-cuff pulse oximeter may be used instead of telemetry ECU recordings. This is necessitated by the fact that a telemetry ECG sensor is too large and heavy (~5 grams) for a 1.5 month old Akita mouse which weighs ~16 grams. The HRV measurements are derived from RR intervals which can also be accurately extracted from pulse intervals from a pulse oximeter. Another advantage of using a pulse oximeter for HRV measurement is that surgical procedures are not needed to implant a PPG sensor. Using PEG recordings, the onset of DCAN in Akita mice can be discerned starting at 3 months which is corroborated by the Western blot analysis.

Reduced heart rate variability is known to be one of the earliest indicators of DCAN (11) in human as it involves an imbalance of the autonomic nervous system (ANS) in humans. Sustained hyperinsulinemic hypoglycemia in type 1 diabetics and their non-diabetic counterparts has been shown to result in reduced cardiac vagal outflow in all patients. One of the consequences of hyperinsulinemic hypoglycemia is decreased autonomic function present in the early development of diabetes, but moreover, prolonged diabetes leads to a progressive decline in autonomic function (13). These human studies clearly indicate autonomic imbalance with only either parasympathetic or sympathetic nervous tone reduced. This is similar to the current study with the PSD method: consistent depression of the two branches of the autonomic nervous system is not often found.

The computational results based on the PDM approach indicate a significant cardiac autonomic impairment in diabetic Akita mice, a model of insulin-dependent type I diabetes. Both immunohistochemical and Western blot analyses show a progressive reduction in autonomic nerve density in Akita mice as compared to the control mice starting at 3 months of age, thus corroborating the PDM data analysis of HRV records. Utilizing a simple measurement based on tail-cuff pulse oximeter recordings, one can determine that the onset of DCAN in Akita mice occurs at 3 months and that the neuropathy persists over time. Given that all that is required for the PDM analysis is either pulse or heart rate intervals, a recent advance in which a smart phone may be used to record pulse intervals suggests that an inexpensive device can be utilized for detection of DCAN in humans. Further, a smart phone camera can be used to detect pulsatile signals from the fingertip that can be used to extract heart rate, respiratory rate, oxygen saturation, as well as autonomic nervous function. Unlike others, the approach of the present disclosure uses standard phone components and does not require extra hardware; the optical video monitoring of the skin with a standard smart phone digital camera is sufficient to detect variability in the heart rate signal and obtain accurate RR interval data. This technology may provide patients easy access and a simple approach for daily monitoring of the progression and onset of DCAN just by placing their fingertip on a video camera of a smart phone.

In one or more embodiments, the system of these teachings for physiological parameter monitoring includes a physiological indicator signal sensing component (sensor) and a mobile communication device having an analysis component analyzing the physiological indicator signal to obtain measurements of one or more physiological parameters.

In one instance, the mobile communication device includes one or more processors and one or more computer usable media, where the computer usable media has computer readable code embodied therein that causes the processor to process the collected data to extract primary and secondary components of the collected data by performing a principal dynamic mode (PDM) analysis, wherein a significant reduction of the primary or secondary component at a predetermined time period is indicative of the DCAN development. In one or more embodiments, the computer readable code causes the processor to implement the methods described hereinabove. The computer usable media can also provide a medium for storing data that can be retrieved by the processor.

It should be noted that other embodiments of the mobile communication device, such as the use of ASICs or FPGAs in order to implement the analysis component are within the scope of these teachings.

Figure 7:
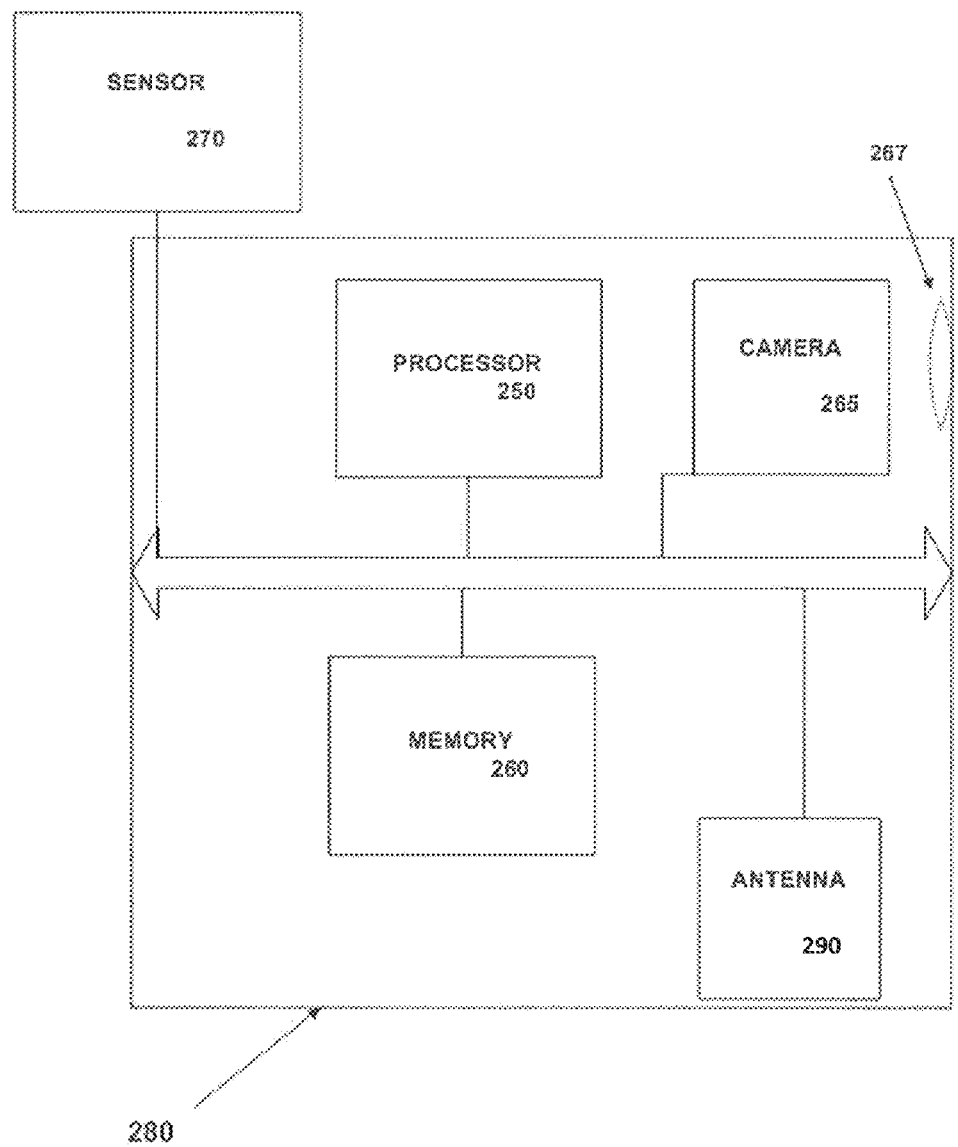
FIG. 7 is a block diagram representation of one embodiment of the system of these teachings.

FIG. 7 is a block diagram representation of one embodiment of the system of these teachings. Referring to FIG. 7, in the embodiment shown therein, a mobile communication system 280 includes a processor 250 and one or more memories 260. A physiological indicator signal sensing component (sensor) 270 supplies a physiological indicators signal to the mobile communication device 280. The sensor 270 can be a photoplethysmographic (PPG) sensor or an electrocardiogram (EKG) sensor. In the embodiment shown in FIG. 7, a camera 265, where the camera as an objective lens 267, can also supply the physiological indicators signal to the mobile communication device 280. The one or more memories 260 have computer usable code embodied therein that causes the processor 250 to that causes the processor to analyze the physiological indicator signal to obtain measurements of one or more physiological parameters and to detect effects of motion artifacts in the measurements of the one or more physiological parameters. In one or more instances, the computer readable code causes the processor 250 to perform the implement the methods described hereinabove.

The one or more memories 260 represent one embodiment of computer usable media having computer readable code embodied therein that causes a processor to implement the methods of these teachings. Embodiments of the method of these teachings are described hereinabove and the computer readable code can cause a processor to implement those embodiments.

In the embodiment shown in FIG. 7, the mobile communication device 280 also includes an antenna 290 that enables communications through one or more of a variety of wireless protocols or over wireless networks. It should be noted that, although the sensor 270 is shown as being directly connected to the mobile communication device 280, embodiments in which the sensor 270 provides the physiological indicators signal to the mobile communication device 280 through a wireless connection are also within the scope of these teachings.

According to a recent study by the subcommittee panel on diabetic neuropathy, it is suggested that a cost-effective approach for DCAN is lacking. Further, diabetic neuropathy, long considered a disease of the peripheral nervous system is now believed to involve the central nervous system. Therefore, embodiments of the present disclosure provide the basis for prospective clinical and basic science studies of a new non-invasive high-throughput tool for the detection of DCAN.

For the purposes of describing and defining the present teachings, it is noted that the term "substantially" may be utilized herein to represent the inherent degree of uncertainty that may be attributed to any quantitative comparison, value, measurement, or other representation. The term "substantially" may also be utilized herein to represent the degree by which a quantitative representation may vary from a stated reference without resulting in a change in the basic function of the subject matter at issue.

Further, for the purposes of describing and defining the present teachings, it is noted that the term "configured to" may be utilized herein to represent a computer usable media having computer readable code embodied therein, the computer readable code being executed in a processor to perform certain method steps.

Although embodiments of the present invention has been described in detail, it is to be understood that these embodiments are provided for exemplary and illustrative purposes only. Various modifications and changes may be made by persons skilled in the art without departing from the spirit and scope of the present disclosure as defined in the appended claims.

What is claimed is:

1. A method for identifying development of diabetic cardiovascular autonomic neuropathy (DCAN) in a biological subject, the method comprising:
   collecting data associated with heart rates of a biological subject; and
   processing the collected data to extract primary and secondary components of the collected data by performing a principal dynamic mode (PDM) analysis;
   determine whether there is a significant reduction of the primary or secondary component at a predetermined time period;
   wherein the significant reduction of the primary or secondary component at the predetermined time period is indicative of the DCAN development.

2. The method of claim 1, wherein the primary and secondary components respectively represent sympathetic and parasympathetic dynamics of an autonomic nervous system of the biological subject.

3. The method of claim 1, wherein collecting the data comprises monitoring pulsatile signals associated with the heart rates of the biological subject by detecting an optical property associated with a biological fluid of the biological subject using an imaging device of a portable communication device.

4. The method of claim 1, wherein collecting the data comprises monitoring pulsatile signals associated with the heart rates of the biological subject by using an electrocardiography (ECG) device.

5. The method of claim 1, wherein processing the collected data comprises using a computing device to:
   detrend the collected data to obtain output data;
   delay the detrended data by one unit to obtain input data;
   form a principal matrix using Volterra kernels based on the input and the output; and
   eigendecompose the principal matrix using a predetermined number of orthonormal functions as a basis to obtain eigenvalues and eigenvectors of the principal matrix.

6. The method of claim 5, wherein the primary and secondary, components respectively correspond to two of the eigenvectors associated with the first two greatest eigenvalues of the principal matrix.

7. The method of claim 5, wherein the orthonormal functions comprise Laguerre functions.

8. The method of claim 1, wherein collecting the data comprises collecting the data while the biological subject is at an active state; and wherein a significant reduction of the primary component is indicative of the DCAN development.

9. The method of claim 1, wherein collecting the data comprises collecting the data while the biological subject is at a quiet state; and wherein a significant reduction of the secondary component is indicative of the DCAN development.

10. A device for identifying development of diabetic cardiovascular autonomic neuropathy (DCAN) in a biological subject, the device comprising:
    a processor configured to collect data associated with heart rates of a biological subject; and
    a memory coupled to the processor to store the collected data;
    wherein the processor is further configured to process the collected data to extract primary and secondary components of the collected data by performing a principal dynamic mode (PDM) analysis; and determine whether there is a significant reduction of the primary or secondary component at a predetermined time period; wherein the significant reduction of the primary or secondary component at the predetermined time period is indicative of the DCAN development.

11. The device of claim 10, wherein the primary and secondary components respectively represent sympathetic and parasympathetic dynamics of an autonomic nervous system of the biological subject.

12. The device of claim 10, further comprising an imaging device coupled to the processor, the imaging device being configured to obtain pulsatile signals associated with the heart rates of the biological subject.

13. The device of claim 12, wherein the imaging device is further configured to detect an optical property associated with a biological fluid of the biological subject so as to obtain the pulsatile signals.

14. The device of claim 10, further comprising an electrocardiography (ECG) device configured to obtain pulsatile, signals associated with the heart rates of the biological subject.

15. The device of claim 10, wherein the processor is further configured to:
   detrend the collected data to obtain output data;
   delay the detrended data by one unit to obtain input data;
   form a principal matrix using Volterra kernels based on the input and the output; and
   eigendecompose the principal matrix using a predetermined number of orthonormal functions as a basis to obtain eigenvalues and eigenvectors of the principal matrix.

16. The device of claim 15, wherein the primary and secondary components respectively correspond to two of the eigenvectors associated with the first two greatest eigenvalues of the principal matrix.

17. The device of claim 15, wherein the orthonormal functions comprise Laguerre functions.

18. The device of claim 10, wherein the processor is further configured to display an indication of the DCAN development, if the processor collects the data while the biological subject is at an active state, and if a significant reduction of the primary component occurs.

19. The device of claim 10, further comprising a display screen configured to display an indication of the DCAN development, if the processor collects the data while the biological subject is at a quiet state, and if a significant reduction of the secondary component occurs.

20. A system for identifying development of diabetic cardiovascular autonomic neuropathy (DCAN) in a biological subject comprising:
   a mobile communication device comprising:
      an imaging device, the imaging device being configured to obtain pulsatile signals associated with the heart rates of the biological subject;
      a processor configured to collect data associated with heart rates of a biological subject; and
      a memory coupled to the processor to store the collected data;
         wherein the processor is further configured to process the collected data to extract primary and secondary components of the collected data by performing a principal dynamic mode (PDM) analysis; and determine whether there is a significant reduction of the primary or secondary component at a predetermined time period; the processor being operatively coupled to the imaging device and the memory;
         wherein the significant reduction of the primary or secondary component at the predetermined time period is indicative of the DCAN development.

21. The system of claim 20 wherein the imaging device is further configured to detect an optical property associated with a biological fluid of the biological subject so as to obtain the pulsatile signals.

22. The system of claim 20 further comprising an electrocardiography (ECU) device configured to obtain pulsatile signals associated with the heart rates of the biological subject.

23. The system of claim 20 wherein the imaging device is further configured to obtain pulsatile signals associated with the heart rates of the biological subject.

24. The system of claim 20 wherein the processor is further configured to display an indication of the DCAN development, if the processor collects the data while the biological subject is at an active state, and if a significant reduction of the primary component occurs.

* * * * *

UNITED STATES PATENT AND TRADEMARK OFFICE
CERTIFICATE OF CORRECTION

| | | |
|---|---|---|
| PATENT NO. | : 8,909,328 B2 | Page 1 of 1 |
| APPLICATION NO. | : 13/950548 | |
| DATED | : December 9, 2014 | |
| INVENTOR(S) | : Ki H. Chon | |

It is certified that error appears in the above-identified patent and that said Letters Patent is hereby corrected as shown below:

In the Claims,

In column 20, lines 24-25 (claim 6), "secondary, components" should read -- secondary components --

In column 22, line 21 (claim 22), "(ECU)" should read -- (ECG) --

Signed and Sealed this
Seventeenth Day of March, 2015

Michelle K. Lee
*Director of the United States Patent and Trademark Office*